(12) United States Patent
Kaesler et al.

(10) Patent No.: US 6,183,794 B1
(45) Date of Patent: Feb. 6, 2001

(54) PROPIONIC ACID, AMMONIA, PROPANEDIOL AND WATER SOLUTIONS AND THE USE THEREOF

(75) Inventors: Bruno Kaesler, Ludwigshafen; Hans Müschen, Maxdorf; Harald Streicher, Ludwigshafen; Wolfgang Samson, Münster, all of (DE)

(73) Assignee: BASF Aktiengesellschaft, Lugwigshafen (DE)

( * ) Notice: Under 35 U.S.C. 154(b), the term of this patent shall be extended for 0 days.

(21) Appl. No.: 09/380,968

(22) PCT Filed: Mar. 17, 1998

(86) PCT No.: PCT/EP98/01373

§ 371 Date: Sep. 14, 1999

§ 102(e) Date: Sep. 14, 1999

(87) PCT Pub. No.: WO98/42205

PCT Pub. Date: Oct. 1, 1998

(30) Foreign Application Priority Data

Mar. 21, 1997 (DE) ................................. 197 12 040
May 12, 1997 (DE) ................................. 197 19 412

(51) Int. Cl.$^7$ ................ A23K 3/00; A23L 3/34; A23B 4/14
(52) U.S. Cl. ................ 426/335; 426/623; 426/630; 426/635; 426/807
(58) Field of Search ................ 426/335, 623, 426/630, 807, 635

(56) References Cited

U.S. PATENT DOCUMENTS

| 3,961,092 | * | 6/1976 | Forest et al. | 426/331 |
| 3,962,475 | * | 6/1976 | Forest et al. | 426/331 |
| 4,223,045 | | 9/1980 | Fink | 426/335 |
| 4,806,353 | | 2/1989 | Thomas | 424/141 |
| 4,847,067 | | 7/1989 | Thomas | 424/639 |

FOREIGN PATENT DOCUMENTS

| 2019125 | 4/1970 | (DE). |
| 2019972 | 4/1970 | (DE). |
| 2655351 | 4/1978 | (DE). |
| 3500187 | 7/1985 | (DE). |
| 195 34 490 | 3/1997 | (DE). |
| 297 12 131 U | 2/1998 | (DE). |
| 122979 | 10/1984 | (EP). |
| 241400 | 10/1987 | (EP). |
| 411827 | 2/1991 | (EP). |
| 1339033 | 11/1973 | (GB). |
| 2153670 | 8/1985 | (GB). |

* cited by examiner

Primary Examiner—Chhaya D. Sayala
(74) Attorney, Agent, or Firm—Keil & Weinkauf

(57) ABSTRACT

The disclosure is directed to a solution of
78.0–93.0% by weight propionic acid,
0.5–5.0% by weight ammonia,
1.0–6.0% by weight propanediol,
0.1–10.0% by weight water,
where the amounts of individual components add up to 100% by weight, and its use in livestock nutrition.

7 Claims, No Drawings

PROPIONIC ACID, AMMONIA, PROPANEDIOL AND WATER SOLUTIONS AND THE USE THEREOF

The present invention relates to solutions of propionic acid, ammonia, propanediol and water, with or without other auxiliaries, and to their use in livestock nutrition.

The use of propionic acid and its salts or esters as preserving additive to feedstuffs of a wide variety of types has been known for a long time (DE-A 20 19 125, DE-A 20 19 972). It is particularly used to preserve feedstuffs such as compound feeds and cereals, legumes or residues from human food. The effect of propionic acid and its salts derives from their biocidal and long-lasting biostatic effect (Zbl. Bakt. II, 125 (1970) 100).

When pure propionic acid is used as preservative, the storage and use are made difficult by the corrosive effect and the unpleasant odor of the acid. Because of these disadvantages, the pure acid is in many cases replaced by its salts, especially the sodium or calcium salt, or its esters. The disadvantage of using the salts or esters is that a considerable part of the biocidal and biostatic activity of propionic acid is lost.

EP-B-0 122 979 discloses the dehydrating effect of virtually anhydrous propylene glycol in the preservation of fish feed. To prevent moldiness, 0.1% by weight of calcium propionate is also added to the fish feed. The method described for the preservation of fish feed is unsuitable for preserving other livestock feeds because of the large amount of propylene glycol (17 to 50% of the weight of the feed) and the small amount of propionic acid.

DE-A 35 00 187 describes a stable pharmaceutical product for treating ketosis in calving cattle, consisting of calcium propionate, dextrose, propylene glycol and other additives such as vitamins, mineral salts and/or amino acids.

EP-A-0 241 400 discloses aqueous solutions of ammonium propionate, which was prepared by mixing 2 mol of propionic acid with 1 mol of ammonium bicarbonate, and at least 5% by weight of propylene glycol. The disadvantage of these aqueous solutions is that their water content is at least 15% by weight, which is too high for concentrated use of ammonium propionate in feed preservation, which reduces the effectiveness of the propionic acid.

DE-A 26 44 351 describes liquid mixtures of ammonium propionate, propylene glycol and water, where the ammonium propionate:propylene glycol molar ratio is from 1:0.1 to 1:0.7 and the ammonium propionate:water molar ratio is from 1:2.0 to 1:3.5. The water content of the liquid mixture is thus in the range from 20 to 30% by weight and is too high for wide use of the preservative. An increasing residual moisture content of the feedstuff to be preserved means that a distinct increase in the amounts used is necessary.

Owing to this and owing to the high water content, the solutions described in EP-A 0 241 400 and DE-A 26 44 351 can be used reliably for preservation of feedstuffs only if their residual moisture content does not exceed 20%. If the residual moisture content of the feed is higher, spoilage often occurs.

For optimal preservation of the feedstuffs, the preservative should have a number of beneficial properties, such as 1. little or no corrosive effect
2. large and/or long-lasting biocidal and/or biostatic effect
3. preservative easy to use (for example good miscibility with the foodstuffs to be preserved)
4. reduced odor (ie. low vapor pressure of the preservative over the solution)
5. minimal water content (ie. small amount used, high activity)
6. little or no damage to materials (ie. no damage to seals, valves and other items).
7. no freezing of the preservative at low temperatures
8. adequate reduction in the pH of the foodstuff to be preserved.

It is an object of the present invention to provide preservative solutions which have little or no corrosive effect, little or no odor and have a high activity, but, on the other hand, have a freezing point which is sufficiently low for practical purposes.

We have found that this object is achieved by a solution consisting essentially of 78.0–93.0% by weight propionic acid,
0.5–5.0% by weight ammonia,
1.0–6.0% by weight propanediol,
0.1–10.0% by weight water, where the amounts of individual components add up to 100% by weight.

A preferred embodiment is a solution consisting essentially of a) 92% by weight propionic acid,
3% by weight ammonia,
4% by weight propanediol and
1% by weight water
b) with or without other auxiliaries.

Another preferred embodiment is a solution consisting essentially of a) 90% by weight propionic acid,
3% by weight ammonia,
4% by weight propanediol and
1% by weight water and
2% by weight surface-active substance
b) with or without other auxiliaries.

Another preferred embodiment is a solution consisting essentially of a) 93% by weight propionic acid,
3% by weight ammonia,
4% by weight propanediol
b) with or without other auxiliaries.

The solutions according to the invention contain 78–93% by weight propionic acid, preferably 85–93% by weight, particularly preferably 87–92% by weight.

The ammonia is present in the solutions in the range from 0.5 to 5.0% by weight, preferably between 2.0 to 4.0% by weight.

Propanediol means propylene glycol and trimethylene glycol, which are advantageously present in the solution in the range from 1 to 6% by weight, preferably between 1 to 4% by weight, particularly preferably between 2 to 4% by weight.

For high biological activity of the solutions, their water content is advantageously 10% by weight or less, and can even be 0% by weight, preferably 0.1 to 6% by weight, particularly preferably 1 to 3% by weight.

The solutions according to the invention may additionally contain surface-active substances and/or at least one other $C_1$–$C_8$-carboxylic acid such as formic acid, acetic, isobutyric, n-butyric, n-valeric, 2-methylbutyric, levulinic, sorbic, benzoic, acrylic and methacrylic acids, and the alkali metal or alkaline earth metal salts thereof customary in agriculture, and the ammonium salts thereof or mixtures thereof, advantageously using as other acid formic acid or acetic acid and/or salts thereof.

Examples of suitable surface-active substances are all anionic, cationic, amphoteric or non-ionic surfactants or mixtures thereof, as long as they are suitable for livestock nutrition, such as polyglycol esters, polyglycerol ethers of fatty alcohols, sugar esters (esters of, for example, sucrose and edible fatty acids), sugar glycerides (mixtures of sucrose esters and mono- and diglycerides of sucrose), polyoxyethylene/polyoxypropylene copolymers (average molecular weight from 6800 to 9000), glycerol mono-, di- or triesters such as mono- and diglycerides of edible fatty acids with lower carboxylic acids such as citric acid, acetic acid, lactic acid, monoacethyl- and diacetyltartaric acid, tartaric acid or mono- and diglycerides with edible fatty acids, sorbitan esters or ethoxylates, fatty acid ester ethoxylates, ethoxylated alkyl ethers of higher fatty acids or lecithin.

Examples of surface-active substances which may be mentioned are substances such as the various Brij® types, ie. cetyl, lauryl, oleyl or stearyl ethers with 2 to 100 polyoxyethylene units, the various Myrj® types [lacuna] stearin esters with 8 to 100 polyoxyethylene units (=POE), the various Span® types such as Span 20 (sorbitan monolaurate), Span 40 (sorbitan monopalmitate), Span 60 (sorbitan monostearate) or Span 80 (sorbitan monooleate), the various Tween® types such as Tween 20 (POE(20) sorbitan monolaurate), Tween 40 (POE(20) sorbitan monopalmitate), Tween 60 (POE(20) sorbitan monostearate) or Tween 80 (POE(20) sorbitan monooleate), the various Triton® types (octylphenol ethoxylates) such as Triton X-15, X-35, X-100 CG, X-305 (70%), X-405 (70%), X-705 (70%), the ethoxylated castor oils such as polyoxyethylene glycerol triricinoleate 35 (Cremophor® EL) or polyoxyethylene glycerol trihydroxystearate 40 (Cremophor® RH40), the ethoxylated 12-hydroxystearic acids such as polyoxyethylene 660 12'-hydroxystearate (Solutol® HS15) or sodium lauryl sulfate. Preference is given to polyoxyethylene 20 sorbitan monopalimitate, polyoxyethylene 20 sorbitan monostearate, polyoxyethylene sorbitan tristearate, sorbitan monolaurate, -oleate, -palmitate, sorbitan tristearate, sugar esters, sugar glycerides, polyglycerol ethers of fatty alcohols, and the ethoxylated castor oils (Cremophor® types).

Auxiliaries which can be added to the solutions according to the invention are all auxiliaries customary in agriculture, such as flavorings, colorings, appetite stimulants, antibiotics, probiotics and/or enzymes. The auxiliaries are advantageously added in an amount of from 0.01% to 10% of the weight of the solution or of the weight of the preservative (component a), preferably in an amount of from 0.1 to 1% by weight.

The solutions according to the invention can be prepared by treating the propionic acid with gaseous ammonia and/or aqueous ammonia solution so that the stated ratios by weight are reached. On use of gaseous ammonia it is advantageous for the ammonia to be blown into the acid through a sintered disk, a filter or a permeable membrane, preferably while stirring the acid. It is also possible, starting from the ammonium salt of the acid, to add further free acid until the required ratio by weight is reached. Water can, if necessary, be added to reach the stated weight. The propanediol and the surface-active substance can be added together or singly to the acid before or after the partial neutralization with ammonia.

The solutions according to the invention are used in livestock nutrition, especially as additive to feed for pigs, piglets and poultry, such as chickens and turkeys. They are particularly suitable for preserving animal feed, preferably liquid feed and compound feed, from unwanted microbial decomposition. The solutions according to the invention have not only a pH-lowering and biocidal, biostatic effect but also a nutritional effect which is attributable in particular to the carboxylic acids such as propionic acid or formic acid and which is particularly beneficial in pig feeding.

The solutions according to the invention are advantageously suitable for preserving compound feed and non-compound feed such as feed cereals such as wheat, oats, rye, barley, and legumes, corn, corncob mix, byproducts from breweries and dairies, and for compound feed preservation or for preserving liquid feed.

The solutions are also suitable, alone or in combination with lactic acid bacteria, for preserving byproducts from abattoirs or sugar production.

The solutions according to the invention can also be employed as additive for preserving and/or disinfecting the drinking water used in livestock nutrition.

Further advantageous applications of the solutions according to the invention are to prevent secondary heating up of feedstuffs, complete treatment and/or surface treatment before preservation of the feedstuffs, and treatment of the cut surface of feedstuffs after opening the preserved feedstuffs.

Another application of the solutions according to the invention is in the production of silage (ensiling). In silage, the required lactic acid fermentation is frequently accompanied by unwanted microbial decomposition, especially by molds and putrefactive bacteria. The solutions according to the invention can be added to the animal feed to prevent this unwanted putrefaction.

The advantageous amounts used of the solutions according to the invention differ according to the residual moisture content of the feedstuff and the required duration of preservation. As a rule, it is sufficient to add 0.1–10 kg of solution per metric tonne of animal feed for successful preservation. The solutions are preferably added in amounts of 0.5–4.5 kg per metric tonne of animal feed. It is possible with this dosage reliably to preserve feedstuffs such as cereals, broad beans, corn, oilseed rape or peas up to a residual moisture content of 50%.

The solutions according to the invention can be added to the feedstuffs or feedstuff mixtures in a manner known per se. The addition to the feedstuff can take place immediately after harvesting or production in the form of the solutions according to the invention, or in the form of particles or porous carriers to which the solutions have initially been applied. These particles or carriers are in this case mixed with the feedstuff. Examples of suitable particles or carriers are vermiculite, pumice or dried sugar beet pulp. The solutions according to the invention can advantageously be added via a metering device to the feedstuff while the feed is being conveyed by a screw into the silo.

The solutions according to the invention are suitable, for example, for preserving grass, agricultural crop plants and/ or mixed livestock nutrition and the materials used for producing them, such as barley, wheat, rye, oats, corn, rice, oilseed rape, legumes, sunflower seeds, soybeans, sugar beet and sugar cane and residues thereof, hay, straw, peanuts, fishmeal, meat or bonemeal.

The solutions according to the invention have the following properties:

They have a pH in the range of from 3.5 to 4.5.

Their freezing points are below 0° C., and freezing points of preferred solutions are below −20° C. and of particularly preferred ones are below −25° C.

Their density (20° C.) is 1.01–1.2 g/ml.

The viscosity at 20° C. is in the range from 5 to 35 mm$^2$/s

EXAMPLES

Example 1

The following solution A was used to preserve wheat with a residual moisture content of 20%.

Solution A

90% by weight propionic acid,

3% by weight ammonia,

4% by weight propanediol and

1% by weight water and

2% by weight Cremophor® EL pH 3.8 to 4

The duration of preservation in the examples was determined, unless indicated otherwise, in an incubator at 25° C with a relative humidity of 80%. The spoilage of the samples was determined from the $CO_2$ concentration over the preserved material. The sample is spoiled if the $CO_2$ concentrations over the preserved material exceed 1%. The duration of prevention of spoilage compared with the control is decisive for the preservation line.

TABLE I

Duration of preservation compared with control without treatment

| Type of treatment | Stability (in weeks) | Difference from control (in weeks) |
|---|---|---|
| Control without treatment | 2 | — |
| 0.10% solution A | 2 | — |
| 0.15% solution A | 3 | 1 |
| 0.20% solution A | 7 | 5 |
| 0.25% solution A | 7 | 5 |
| 0.10% pure propionic acid | 2 | — |
| 0.15% pure propionic acid | 3 | 1 |
| 0.20% pure propionic acid | 7 | 5 |
| 0.25% pure propionic acid | 7 | 5 |
| 0.15% solution X | 2 | — |

TABLE I-continued

Duration of preservation compared with control without treatment

| Type of treatment | Stability (in weeks) | Difference from control (in weeks) |
|---|---|---|
| 0.20% solution X | 2 | — |
| 0.25% solution X | 3 | 1 |
| 0.30% solution X | 7 | 5 |
| 0.35% solution X | 7 | 5 |

Solution X = 64% by weight propionic acid, 7.5% by weight $NH_3$, remainder water, pH 5.0

Example 2

The following solution B was used to preserve wheat with a residual moisture content of 20%.

Solution B 77.4% by weight propionic acid 11.6% by weight formic acid

5% by weight ammonia,

4% by weight 1,2-propanediol and

2% by weight water

TABLE II

Duration of preservation of various products

| Dosage in % | pure propionic acid | Solution B | Solution X |
|---|---|---|---|
| 0.1 | — | 1 week | — |
| 0.15 | 1 week | 1 week | — |
| 0.20 | 5 weeks | 2 weeks | — |
| 0.25 | 5 weeks | 5 weeks | 1 week |
| 0.30 | n.m. | 5 weeks | 5 weeks |
| 0.35 | n.m. | n.m. | 5 weeks | n.m. = not determined

Example 3

The following solution C was used to preserve compound feed with a residual moisture content of 19% (Piglet starter feed).

Solution C

76% by weight propionic acid,

12% by weight formic acid

5% by weight ammonia,

4% by weight 1,2-propanediol, 2.7% by weight water and 0.3% by weight acetic acid

TABLE III

Duration of preservation of various products

| Dosage in % | pure propionic acid | Solution C | Solution X |
|---|---|---|---|
| 0.1 | — | — | — |
| 0.15 | 1 week | — | — |
| 0.20 | 3 weeks | 3 weeks | — |
| 0.25 | 4 weeks | 4 weeks | 2 weeks |
| 0.35 | 5 weeks | 4 weeks | 2 weeks |

Example 4

The following solution D was used to preserve compound feed with a residual moisture content of 19% (Piglet starter feed).

Solution D

93% by weight propionic acid,

3% by weight ammonia,

4% by weight propanediol, pH 4.4

TABLE IV

Duration of preservation of various products

| Dosage in % | pure propionic acid | Solution D | Solution X |
|---|---|---|---|
| 0.1 | — | — | — |
| 0.15 | 1 week | — | — |
| 0.20 | 3 weeks | 2 weeks | — |
| 0.25 | 4 weeks | 4 weeks | 2 weeks |
| 0.35 | 5 weeks | 5 weeks | 2 weeks |

We claim:

1. A solution consisting essentially of 78.0–93.0% by weight propionic acid, 0.5–5.0% by weight ammonia, 1.0–6.0% by weight propanediol, 0.1–10.0% by weight water, with the proviso that the total of the individual components adds up to 100% by weight.

2. The solution of claim 1, which additionally comprises up to 5% by weight of a surface-active substance.

3. The solution of claim 1, which additionally comprises up to 15% by weight of at least one other $C_1$–$C_8$-carboxylic acid.

4. A method of preserving or disinfecting drinking water which comprises adding to the water an effective amount of the solution defined in claim 1.

5. A method of preserving animal feedstuffs, which comprises adding to a feedstuff or a feedstuff mixture a solution as defined in claim 1 in amounts of 0.1–10 kg of solution per metric tonne of animal feed.

6. A preservative consisting essentially of a) 92% by weight propionic acid

3% by weight ammonia

4% by weight propanediol

1 % by weight water b) with or without one or more auxiliaries selected from the group consisting of flavorings, colorings, appetite stimulants, antibiotics, probiotics and enzymes.

7. A preservative consisting essentially of a) 90% by weight propionic acid

3% by weight ammonia

4% by weight propanediol

1 % by weight water

2% by weight surface-active substance b) with or without one or more auxiliaries selected from the group consisting of flavorings, colorings, appetite stimulants, antibiotics, probiotics and enzymes.

* * * * *